(12) United States Patent
Qiu

(10) Patent No.: US 7,627,090 B2
(45) Date of Patent: Dec. 1, 2009

(54) CONFIGURATION OF A MEDICAL RADIOTHERAPEUTIC INSTRUMENT

(76) Inventor: Yanxiong Qiu, Block B, Buld. B1, Shenzhen Digital Technical Yard, S. Road 7th, High-Tech Zhon, Shenzhen (CN)

( * ) Notice: Subject to any disclaimer, the term of this patent is extended or adjusted under 35 U.S.C. 154(b) by 120 days.

(21) Appl. No.: 11/837,736

(22) Filed: Aug. 13, 2007

(65) Prior Publication Data

US 2008/0084968 A1 Apr. 10, 2008

(30) Foreign Application Priority Data

Oct. 8, 2006 (CN) .................... 2006 2 0137765 U
Oct. 8, 2006 (CN) .................... 2006 2 0137766 U

(51) Int. Cl.
*G21K 1/04* (2006.01)
*G21F 5/02* (2006.01)
*G21F 5/04* (2006.01)
*G21F 5/015* (2006.01)

(52) U.S. Cl. ........................ 378/150; 378/149; 378/147; 250/498.1; 250/507.1

(58) Field of Classification Search .................... 378/65, 378/147–153, 160; 250/496.1, 497.1, 498.1, 250/505.1, 506.1, 507.1
See application file for complete search history.

(56) References Cited

U.S. PATENT DOCUMENTS

| | | | | |
|---|---|---|---|---|
| 3,254,224 A | * | 5/1966 | Peterson | .................. 250/497.1 |
| 4,190,773 A | * | 2/1980 | Braden et al. | .................. 378/10 |
| 4,513,204 A | * | 4/1985 | Domnanovich et al. | .. 250/496.1 |
| 5,436,958 A | * | 7/1995 | Taylor | ........................ 378/149 |
| 5,479,021 A | * | 12/1995 | Morgan et al. | ......... 250/363.04 |
| 6,389,108 B1 | * | 5/2002 | Ein-Gal | ...................... 378/147 |
| 7,430,280 B2 | * | 9/2008 | Song | .......................... 378/145 |
| 2001/0016028 A1 | * | 8/2001 | Adams et al. | .................. 378/90 |
| 2008/0237473 A1 | * | 10/2008 | Uribe et al. | .............. 250/363.1 |

* cited by examiner

*Primary Examiner*—Edward J Glick
*Assistant Examiner*—Anastasia Midkiff
(74) *Attorney, Agent, or Firm*—Global IP Services; Tianhua Gu

(57) ABSTRACT

A medical radiotherapeutic instrument comprising a ray source body, a switch and an end collimation body, a pre-collimation hole and a ray source cavity for placing ray source are defined on the ray source body; the switch is at least one pillar, each pillar is coupled with a drive unit, the pillars are disposed inside the ray source body, a middle collimation hole is defined on each pillar; under the driving of the drive unit, the pillar arise a displacement to move the middle collimation hole into or out of alignment with the pre-collimation hole; the end collimation body is disposed inside the ray source body, and an end collimation hole is defined on the end collimation body, the end collimation hole is connected with the pre-collimation hole through the middle collimation hole to form a therapy path. The present invention is simplified in structure and low in cost, with this structure, it can control the switch separately, and continuously adjust the radiate amount.

3 Claims, 4 Drawing Sheets

CONFIGURATION OF A MEDICAL RADIOTHERAPEUTIC INSTRUMENT

CROSS REFERENCE TO RELATED PATENT APPLICATION

This application claims the priorities of the Chinese patent application No. 200620137766.5, which has a filing date of Oct. 8, 2006 and the Chinese patent application No. 200620137765.0, which has a filing date of Oct. 8, 2006.

FIELD OF THE INVENTION

The present invention relates to medical equipments, more particularly, relates to a medical radiotherapeutic instrument.

BACKGROUND OF THE INVENTION

A serious complication may be infected by a traditional encephalic surgery and even death may be caused. So years ago, a Swedish professor, Doctor Leksell, first presented a concept of "Stereotactic Radio surgery" (SRS), which is applying the theory of stereotaxic to use high-octane ray focusing irradiation and to destroy targeted organisms, thus to cure the sickness. Such kind of therapy which employ ray to treat an encephalic disease is named as stereotactic radiosurgery science, and it started a new century of no wound radiosurgery.

Ordinarily, a traditional radiotherapeutic instrument comprises of a ray source body, a switch and an end collimation body. FIG. 1 of the drawings shows an embodiment of the radiotherapeutic instrument of prior art, and FIG. 2 is the sectional view of the instrument in FIG. 1. As shown in FIGS. 1 and 2, the radiotherapeutic instrument comprises a ray source body 1 with a ray source cavity 4 and a pre-collimation hole 5 defined on, a switch 2 with a middle collimation hole 8 set on, an end collimation body 3 with an end collimation hole 9 defined on. The pre-collimation hole 5, middle collimation hole 8 and end collimation hole 9 can be connected to form a therapy path. The switch 2 usually is integrated as a whole, the middle collimation hole 8 will be moved into or out of alignment with the pre-collimation hole 5 of the ray resource body by the movement of the switch, therefore to open or close the therapy path. But with this configuration, the radial passageway will be entirely open or closed when switching on/off the ray resource, so the radiate amount can't be adjusted continuously and flexibly.

SUMMARY OF THE INVENTION

The object of the present invention is to provide a medical radiotherapeutic instrument, which is simplify in structure and low in cost, it can control the switch separately, and continuously adjust the radiate amount.

The technical solution of the present invention is, provides a medical radiotherapeutic instrument that comprising a ray source body, a switch and an end collimation body, wherein a pre-collimation hole and a ray source cavity for placing ray source are defined on the ray source body;

the switch is at least one pillar, each pillar is coupled with a drive unit, the pillars are disposed inside the ray source body, a middle collimation hole is defined on each pillar; thereby, the drive unit can drive the pillar to move the middle collimation hole into or out of alignment with the pre-collimation hole;

the end collimation body is disposed inside the ray source body, and an end collimation hole is defined on the end collimation body, the end collimation hole is connected with the pre-collimation hole through the middle collimation hole to form a therapy path.

Preferably, the drive unit is a linear driver to drive the pillar to move linearly to open or close the therapy path.

Preferably, the drive unit is a rotational driver to drive the pillar to move rotationally to open or close the therapy path.

The medical radiotherapeutic instrument of the present invention has the advantages of simplify in structure and low in cost; the linear driver or rotational driver controls each pillar to move forward, backwardly, or rotationally, and makes the middle collimation hole departing from the pre-collimation hole therefore to switch on/off the ray source, and neatly adjust the radiate amount.

BRIEF DESCRIPTION OF THE INVENTION

DETAILED DESCRIPTION OF THE PREFERRED EMBODIMENT

Figure 1:
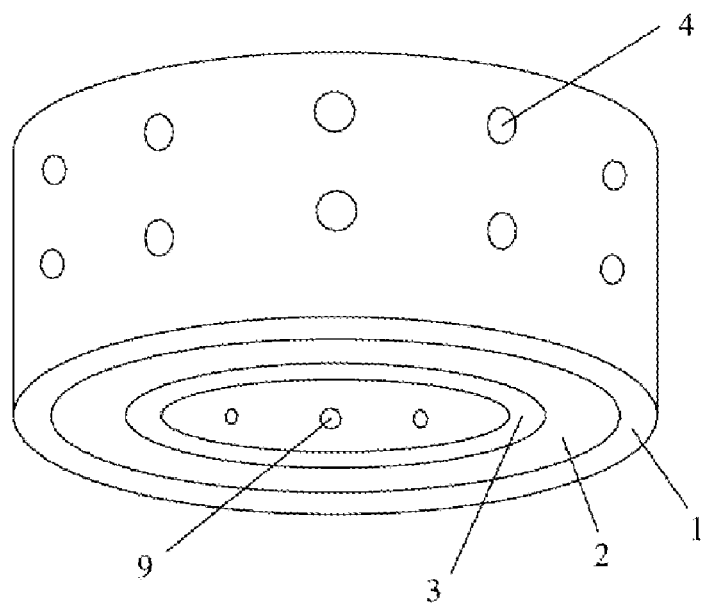
FIG. 1 is the schematic view of the medical radiotherapeutic instrument in the prior art.
Figure 2:
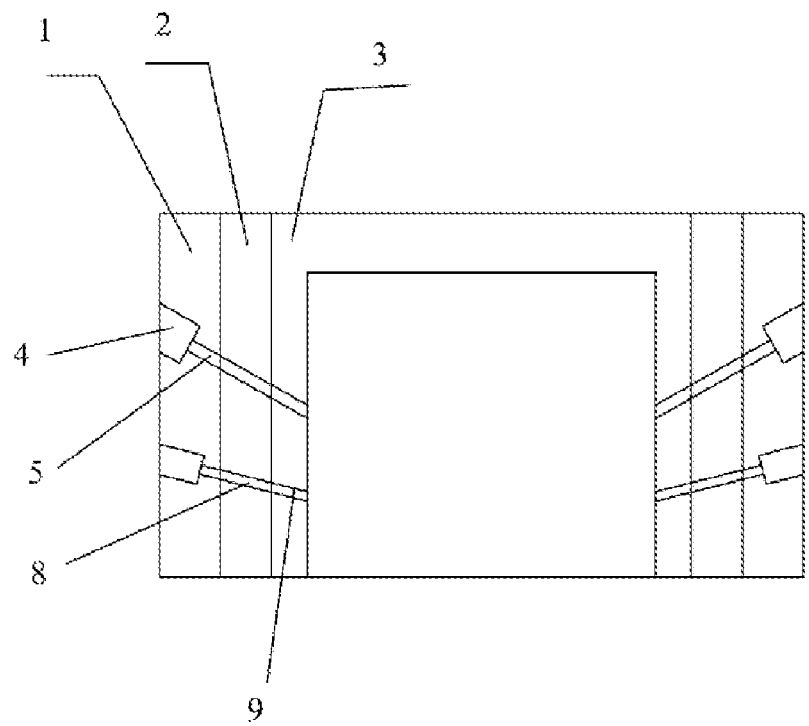
FIG. 2 is the sectional view of the medical radiotherapeutic instrument as in FIG. 1.
Figure 3:
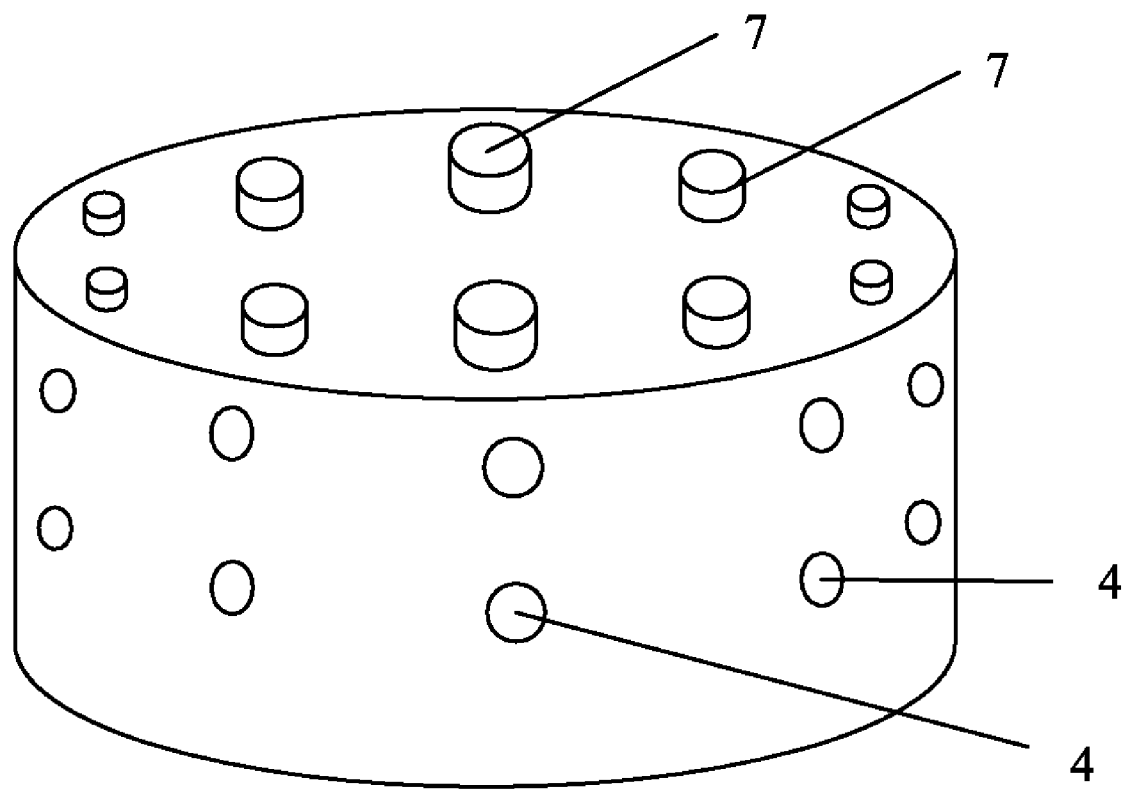
FIG. 3 is the schematic view of one preferred embodiment of the medical radiotherapeutic instrument, in accordance with the present invention.
Figure 4:
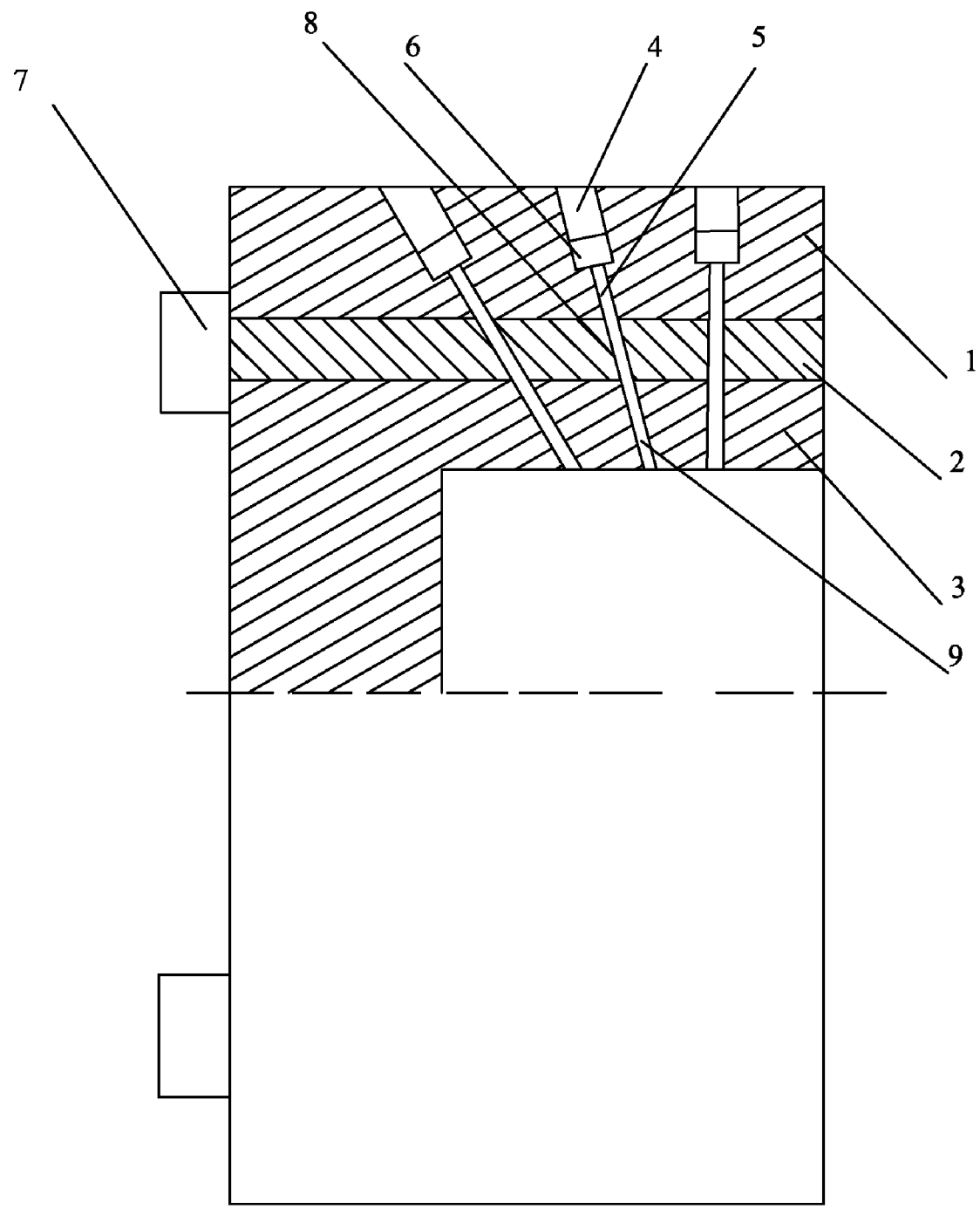
FIG. 4 is the structure view of the medical radiotherapeutic instrument as in FIG. 3.

As shown in FIGS. 3 and 4, one preferred embodiment of the present invention is provided, the medical radiotherapeutic instrument comprises a ray source body 1, a switch 2 and an end collimation body 3, wherein a pre-collimation hole 5 and a ray source cavity 4 for placing ray source are defined on the ray source body 1; the switch 2 is a plurality of pillars that disposed inside the ray source body 1, and on the top end of each pillar, a middle collimation hole 8 is defined, and a drive unit 7 is installed thereon also. The drive unit 7 is a linear driver that can drive each pillar to move forwardly or backwardly, thus to move the middle collimation hole 8 into or out of alignment with the pre-collimation hole 5 of the ray source body 1, as shown in FIG. 1. The end collimation body 3 is disposed inside the ray source body 1, and an end collimation hole 9 is defined on the end collimation body 3.

When in operation, the switch 2 is driven by the drive unit 7 to move the middle collimation hole 8 into or out of alignment with the pre-collimation hole 5, so the pre-collimation hole 5, middle collimation hole 8 and end collimation hole 9 are connected, thus a therapy path is formed. Or, under the driving of the drive unit 7, the switch 2 will make the middle collimation hole 8 to depart from the pre-collimation hole 5, thus to close the therapy path and to neatly adjust the radiate amount.

Figure 5:
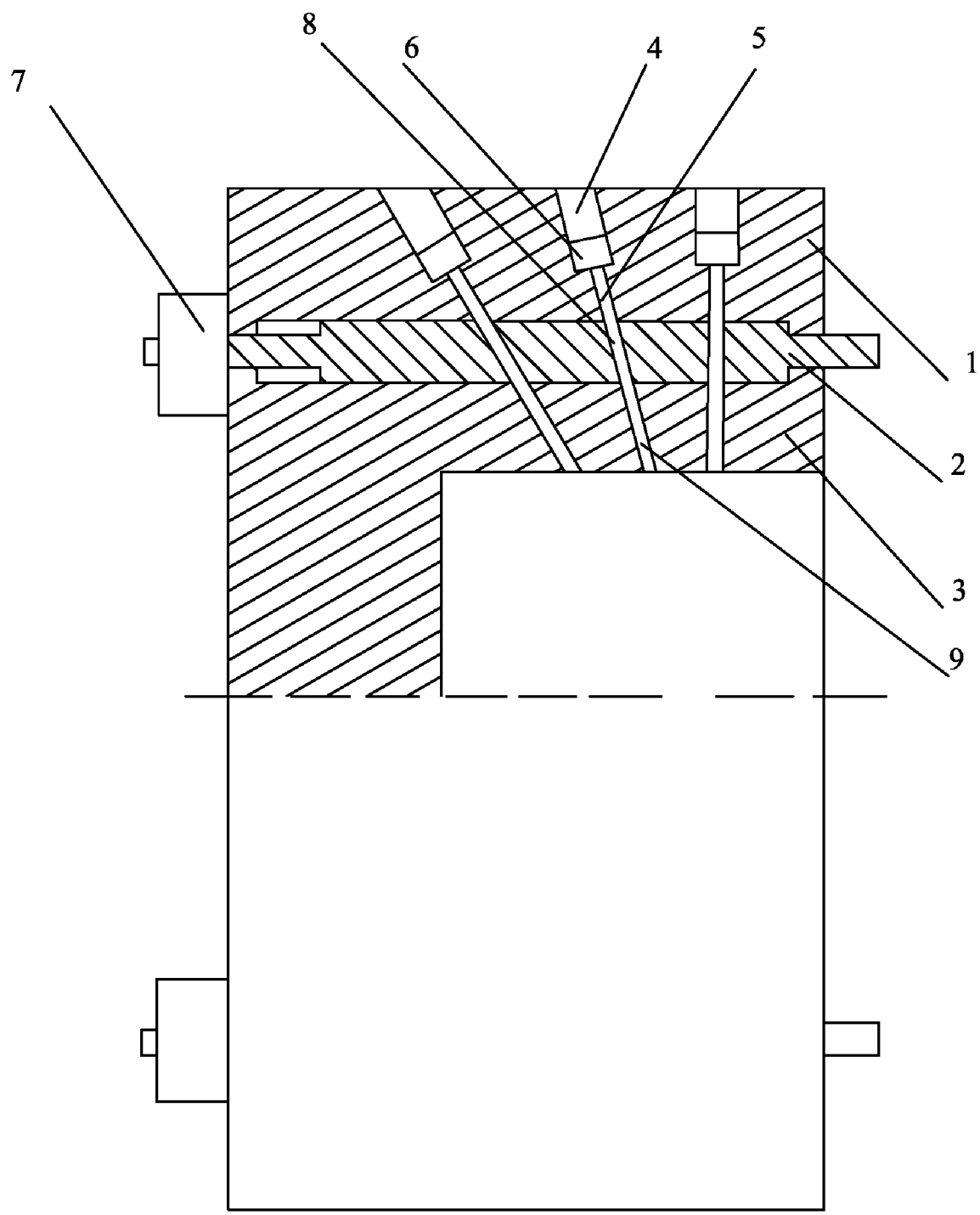
FIG. 5 is the schematic view of another preferred embodiment of the medical radiotherapeutic instrument, in accordance with the present invention.

Another preferred embodiment of the present invention is shown in FIG. 5, in which the switch 2 is at least one pillar that disposed inside the ray source body 1, and on the top end of each pillar, a middle collimation hole 8 is defined, and a drive unit 7 is installed thereon also. The drive unit 7 is a rotational driver that can drive each pillar to move rotationally, thus to move the middle collimation hole 8 into or out of alignment with the pre-collimation hole 5 of the ray source body.

The medical radiotherapeutic instrument of the present invention has the advantages of simplify in structure and low in cost; the linear driver or rotational drive unit 7 controls each pillar to move forwardly, backwardly or rotationally, and makes the middle collimation hole 8 departing from the pre-collimation hole 5 therefore to switch on/off the ray source, and neatly adjust the radiate amount.

Throughout the specification the aim has been to describe the preferred embodiment of the present invention without limiting the invention to any one embodiment or specific collection of features. Persons skilled in the relevant art may realize variations from the specific embodiment that will nonetheless fall within the scope of the invention.

What is claimed is:

1. A medical radiotherapeutic instrument comprising a ray source body, a switch and an end collimation body, wherein:
    a pre-collimation hole and a ray source cavity for placing a ray source are defined on the ray source body;
    the switch being at least two pillars, each pillar of said at least two pillars being coupled with a drive unit, the pillars being disposed inside the ray source body, a middle collimation hole being defined on each pillar of said at least two pillars, thereby the drive unit drives the pillars to move the middle collimation hole into or out of alignment with the pre-collimation hole;
    the end collimation body being disposed inside the ray source body, and an end collimation hole being defined on the end collimation body, the end collimation hole being connected with the pre-collimation hole through the middle collimation hole to form a therapy path.

2. The medical radiotherapeutic instrument as in claim 1, wherein the drive unit is a linear driver to drive each of said at least two pillars to move linearly to open or close the therapy path.

3. The medical radiotherapeutic instrument as in claim 1, wherein the drive unit is a rotational driver to drive each of said at least two pillars to move rotationally to open or close the therapy path.

* * * * *